United States Patent
Reicher et al.

(10) Patent No.: US 11,416,543 B2
(45) Date of Patent: *Aug. 16, 2022

(54) EXAM PREFETCHING BASED ON SUBJECT ANATOMY

(71) Applicant: INTERNATIONAL BUSINESS MACHINES CORPORATION, Armonk, NY (US)

(72) Inventors: Murray Reicher, San Diego, CA (US); Dante Togliatti, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 427 days.

This patent is subject to a terminal disclaimer.

(21) Appl. No.: 15/258,845

(22) Filed: Sep. 7, 2016

(65) Prior Publication Data

US 2018/0068069 A1    Mar. 8, 2018

(51) Int. Cl.
*G06F 16/58* (2019.01)
*A61B 5/055* (2006.01)
(Continued)

(52) U.S. Cl.
CPC ........ *G06F 16/5866* (2019.01); *A61B 5/0033* (2013.01); *A61B 5/055* (2013.01);
(Continued)

(58) Field of Classification Search
CPC ... G06F 19/321; G06F 16/5866; A61B 8/565; A61B 6/566; A61B 5/7435;
(Continued)

(56) References Cited

U.S. PATENT DOCUMENTS 8,190,613 B2 * 5/2012 Takuma ................ G06F 16/313
707/741
8,774,560 B2 7/2014 Sugaya et al.
(Continued)

FOREIGN PATENT DOCUMENTS

CN    105765591    7/2016
GB    2480220    6/2016
(Continued)

OTHER PUBLICATIONS

Varma, "Managing DICOM images: Tips and tricks for the radiologist", 2012, Indian J Radiol Imaging, 22(1): 4-13 (Year: 2012).*
(Continued)

*Primary Examiner* — Christopher L Gilligan
*Assistant Examiner* — Steven G. S. Sanghera
(74) *Attorney, Agent, or Firm* — Erik A. Huestis; Stephen J. Kenny; Foley Hoag, LLP (57) ABSTRACT

Inference of appropriate anatomical region from inconsistent descriptions in order to provide fast and accurate prefetching is provided. In various embodiments, an anatomical region of a first medical imaging study is determined. A first plurality of keywords is determined corresponding to the anatomical region of the first medical imaging study. A plurality of studies is accessed having a patient in common with the first medical imaging study. A second plurality of keywords is extracted from the plurality of studies. Those of the plurality of studies having extracted keywords in common with the first plurality of keywords are selected. The selected studies are pre-fetched for display to a user.

17 Claims, 9 Drawing Sheets

(51) Int. Cl.
*A61B 5/00* (2006.01)
*G16H 50/50* (2018.01)
*A61B 8/00* (2006.01)
*A61B 6/00* (2006.01)
*G16H 30/20* (2018.01)
*G16H 50/70* (2018.01)
*A61B 6/03* (2006.01)

(52) U.S. Cl.
CPC ............ *A61B 5/742* (2013.01); *A61B 5/7435* (2013.01); *A61B 6/566* (2013.01); *A61B 8/565* (2013.01); *G16H 30/20* (2018.01); *G16H 50/50* (2018.01); *G16H 50/70* (2018.01); *A61B 5/0037* (2013.01); *A61B 6/032* (2013.01); *A61B 6/461* (2013.01); *A61B 8/461* (2013.01); *A61B 2576/00* (2013.01)

(58) Field of Classification Search
CPC ....... A61B 5/0033; A61B 5/742; A61B 5/055; A61B 2576/00; A61B 5/0037; A61B 6/032; A61B 8/461; A61B 6/461; G16H 50/50; G16H 30/20; G16H 50/70
See application file for complete search history.

(56) References Cited

U.S. PATENT DOCUMENTS

| | | | |
|---|---|---|---|
| 9,390,236 B2 | 7/2016 | Geller et al. | |
| 2006/0095423 A1 | 5/2006 | Reicher et al. | |
| 2006/0106642 A1 | 5/2006 | Reicher et al. | |
| 2006/0239573 A1 | 10/2006 | Novatzky et al. | |
| 2008/0126982 A1* | 5/2008 | Sadikali | G16H 30/20 715/810 |
| 2008/0140723 A1* | 6/2008 | Hernandez | G06F 19/321 |
| 2008/0262874 A1* | 10/2008 | Toshimitsu | G16H 30/20 705/3 |
| 2009/0228299 A1* | 9/2009 | Kangarloo | G06Q 10/10 705/2 |
| 2011/0066635 A1* | 3/2011 | Moriya | G16H 15/00 707/769 |
| 2012/0254172 A1* | 10/2012 | Bocirnea | G16H 15/00 707/737 |
| 2012/0284657 A1 | 11/2012 | Hafey et al. | |
| 2014/0142980 A1* | 5/2014 | Revell | G16H 10/60 705/3 |
| 2014/0297316 A1 | 10/2014 | Noordvyk | |
| 2016/0292155 A1* | 10/2016 | Adriaensens | G06F 19/321 |
| 2016/0314588 A1 | 10/2016 | Harper | |
| 2017/0206322 A1 | 7/2017 | Kumar | |
| 2017/0337328 A1 | 11/2017 | Ruppertshofen et al. | |

FOREIGN PATENT DOCUMENTS

| | | | |
|---|---|---|---|
| JP | 2001275986 | 10/2001 | |
| WO | WO-2015003748 A1 * | 1/2015 | ............... G06T 7/60 |

OTHER PUBLICATIONS

Zhuang, Y., Jiang, N., Wu, Z. et al. (2014). Efficient and robust large medical image retrieval in mobile cloud computing environment. Information Sciences, 263, 60-86.

Shen, H., Ma, D., Zhao, Y. et al. (2014). MIAPS: A web-based system for remotely accessing and presenting medical images. Computer methods and programs in biomedicine, 113(1).

Sinha et al., "A Review of Medical Imaging Informatics," Annals of the New York Academy of Sciences, 980:168-197 (2002).

* cited by examiner

Region / Exam Type Report

Information

Click Run Report to assess all Exam Types. Try to define rules so each Exam Type is assigned a unique region.
If the report shows Exams Types that are assigned multiple or no regions, use the Define Regions dialog to add, modify, or delete regions or keywords; then run the report again.

Analysis results

| | | | | |
|---|---|---|---|---|
| Unique matches: | 301 | No region in database: | 107 | Total Exam Types: 408 |
| Multiple matches: | 12 | Region in DB matches report: | 301 | |
| No matches: | 95 | Region in DB does not match report: | 0 | |

☑ Show unique matches  ☑ Show multiple matches  ☑ Show unmatched     Copy to Clipboard

| Result | Modality | Region in DB | Region Found | Exam Description | Code |
|---|---|---|---|---|---|
| Unique | CR | HAND OR WRIST | HAND OR WRIST | BONE AGE (HAND) | 10103 |
| Unique | CR | ENTIRE BODY | ENTIRE BODY | OSSEOUS BONE SURVEY COMPLETE | 10106 |
| Unique | CR | CHEST | CHEST | CHEST TWO VIEWS | 11101 |
| Unique | CR | CHEST | CHEST | RIBS UNILATERAL | 11108 |
| Unique | CR | CHEST | CHEST | RIBS BILATERAL | 11110 |
| Unique | CR | CHEST | CHEST | STERNOCLAVICULAR JOINT | 11113 |
| Unique | CR | CHEST | CHEST | CHEST (1 VIEW) | 11115 |
| Unique | CR | ABDOMEN | ABDOMEN | ABDOMEN ONE VIEW (KUB) | 12101 |
| Unique | CR | CHEST / ABDOMEN | CHEST / ABDOMEN | ABDOMEN COMPW/CHEST PA | 12104 |
| Unique | CR | GI | GI | ESOPHAGUS | 12106 |
| Unique | CR | GI | GI | UGI W SMALL BOWEL | 12112 |
| Unique | CR | GI | GI | BARIUM ENEMA | 12115 |
| Unique | CR | GI | GI | BARIUM ENEMA AIR CONTRAST | 12116 |
| Unique | CR | GI | GI | UGI W AIR | 12141 |
| Unique | CR | GI | GI | UGI W AIR AND SMALL BOWEL | 12149 |
| Unique | CR | PELVIS | PELVIS | HYSTEROSALPINGOGRAPHY | 12415 |
| Unique | XA | PELVIS | PELVIS | PELVIC ANGIO | 12467 |

Apply    OK 501
502

EXAM PREFETCHING BASED ON SUBJECT ANATOMY

BACKGROUND

Embodiments of the present invention relate to prefetching examinations, and more specifically, to inferring appropriate anatomical region from inconsistent descriptions in order to provide fast and accurate prefetching.

BRIEF SUMMARY

According to embodiments of the present disclosure, methods of and computer program products for prefetching examinations are provided. In the method, an anatomical region of a first medical imaging study is determined. A first plurality of keywords is determined corresponding to the anatomical region of the first medical imaging study. A plurality of studies is accessed having a patient in common with the first medical imaging study. A second plurality of keywords is extracted from the plurality of studies. Those of the plurality of studies having extracted keywords in common with the first plurality of keywords are selected. The selected studies are pre-fetched for display to a user. In various embodiments, determining the anatomical region of the first medical imaging study includes atlas matching.

In various embodiments, a computer program product for examination prefetching includes a computer readable storage medium having program instructions embodied therewith. The program instructions are executable by a processor to cause the processor to perform a method, which includes determining an anatomical region of a first medical imaging study. A first plurality of keywords is determined corresponding to the anatomical region of the first medical imaging study. A plurality of studies is accessed having a patient in common with the first medical imaging study. A second plurality of keywords is extracted from the plurality of studies. Those of the plurality of studies having extracted keywords in common with the first plurality of keywords are selected. The selected studies are pre-fetched for display to a user. In various embodiments, determining the anatomical region of the first medical imaging study includes atlas matching.

In various embodiments, a system includes an image archive, a display, and a computing node having program instructions embodied therewith. The program instructions are executable by a processor to cause the processor to perform a method, which includes determining an anatomical region of a first medical imaging study. A first plurality of keywords is determined corresponding to the anatomical region of the first medical imaging study. A plurality of studies is accessed having a patient in common with the first medical imaging study. A second plurality of keywords is extracted from the plurality of studies. Those of the plurality of studies having extracted keywords in common with the first plurality of keywords are selected. The selected studies are pre-fetched for display to a user. In various embodiments, determining the anatomical region of the first medical imaging study includes atlas matching.

BRIEF DESCRIPTION OF THE SEVERAL VIEWS OF THE DRAWINGS

FIG. 5 depicts an exemplary report output according to embodiments of the present disclosure.

FIG. 6 depicts an exemplary user interface for configuring pre-fetch rules according to embodiments of the present disclosure.

DETAILED DESCRIPTION

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

Although tagging is available in DICOM, it is used inconsistently across disciplines and sites. Accurate identification of examination type is critical to downstream tasks like report generation, and so inconsistent tagging poses a significant issue in many systems.

In various implementations, the examination type is stored in a database table integral to or separate from the a PACS. System automation and user preferences may all depend on the types of exams in such a table. For example, the exam presentation protocols, which exams are selected for comparison, the attached default report template, patient forms that are presented, and forms for technologists may all require an administrator to set up links between each exam type and other exam types or these other data master files. This leads to significant complexity that can significantly delay deployment of enterprise imaging solutions. In addition, it is a significant source of mistakes and resultant clinical inefficiencies.

As more and more healthcare provider institutions consolidate, the table of available radiology exams often grows. Whereas an ideal radiology practice might include about 30 body parts, and as many as about 600-800 exam types, certain facilities may have 15,000 or more exam types. Setting 5-10 different sets of links between master files that may have several hundred items themselves to each of 15,000 exams types is inefficient and time consuming.

To resolve this problem, the present disclosure provides for examining the language in an exam description and categorizing each exam into a body part. Automatic categorization according to various embodiments is not dependent on the DICOM header file. Instead, language in the exam description is evaluated. In addition, image analytics and deep learning may be applied to even more accurately categorize exams types by body part. Watson image analytics is particularly suitable for such embodiments, as such a machine learning system may be otherwise performing analysis for other purposes.

The present disclosure provides significant benefits by reducing a facility's exam type organization to 30-40 body parts and having all of the various master file links based on body part instead of exam type. In particular, the need to create hundreds of thousands of links manually is reduced by about 98%. The ability to pre-build an entire enterprise imaging system in the factory and then deliver is provided. This approach is more efficient and results in higher quality than a manual approach of shipping hardware and software for configuration in the field.

The present disclosure thus provides a more efficient approach to project management and delivery of image management systems.

According to various embodiments of the present disclosure, prior studies are retrieved for report generation, and are screened based on anatomy. In order to arrive at the relevant anatomy, DICOM fields are tested against a list of strings that are indicative of the actual anatomy, irrespective of any mislabeling. These strings roughly correspond to clinical concepts, and so are resilient indicators of a study's subject. The list of strings may be predetermined manually, or it may be derived through data mining. In addition to manual checking, refiling of images in the course of use can be used as training data.

According to various embodiments of the present disclosure, a UI is also provided for rule creation, allowing the keywords and exam types to be user determined.

According to various embodiments of the present disclosure, a UI is provided for browsing studies, in which a positional indicator is displayed on a schematic image of the body for each available study. This UI may be used for training the system by prompting a user to drag a given image onto the body at the appropriate location.

According to various embodiments set forth herein, DICOM prefetch from external archives is provided. Various systems and methods set out herein have various advantages over alternative approaches. In particular, prefetch is made simpler via a limited number of rules; prefetch is made faster by only running a single query per new exam; prefetch is made accurate by associating a set of pre-defined keywords with each rule; prefetch is made easier to support and configure by eliminating any rule-per-exam-type requirement.

Accordingly, in various embodiments, a small set of rules is created that map any DR exam type to a specific body part and modality that define a single DICOM query. For example, a new "CR Chest" exam may use "CHEST" as the body part and "CR" as the modality. Further discussion of the each rules and body parts is described in further detail below.

In various embodiments, a default set of keywords is provided that is associated with each body part. These defaults can be modified by system administrator and/or service personnel so each site can be optimally configured.

In various embodiments, a DICOM prefetch algorithm is provided that simplifies the DICOM query process by incorporating the above requirements into a single DICOM query per new exam.

In various embodiments, a test bed is provided to verify, validate and optimize pre-defined rules. The rules may still be modifiable, but the more accurate the pre-defined rules are initially, the more that a system can be delivered and considered to be prefetch ready out of the box.

In various embodiments, DICOM prefetch from an external archive is provided as an automatic process, which runs in the background.

Figure 1:
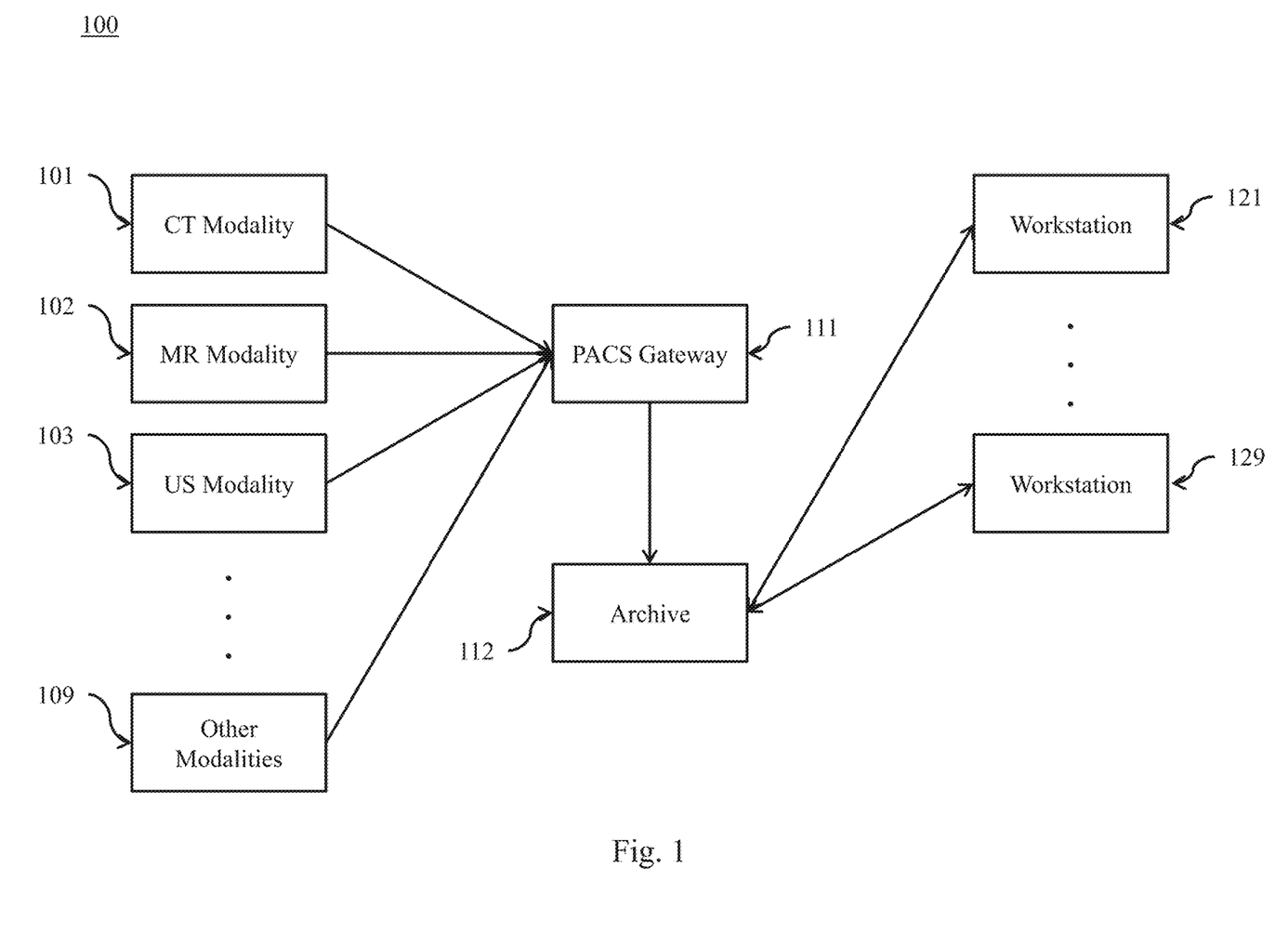
FIG. 1 depicts an exemplary Picture Archiving and Communication System.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
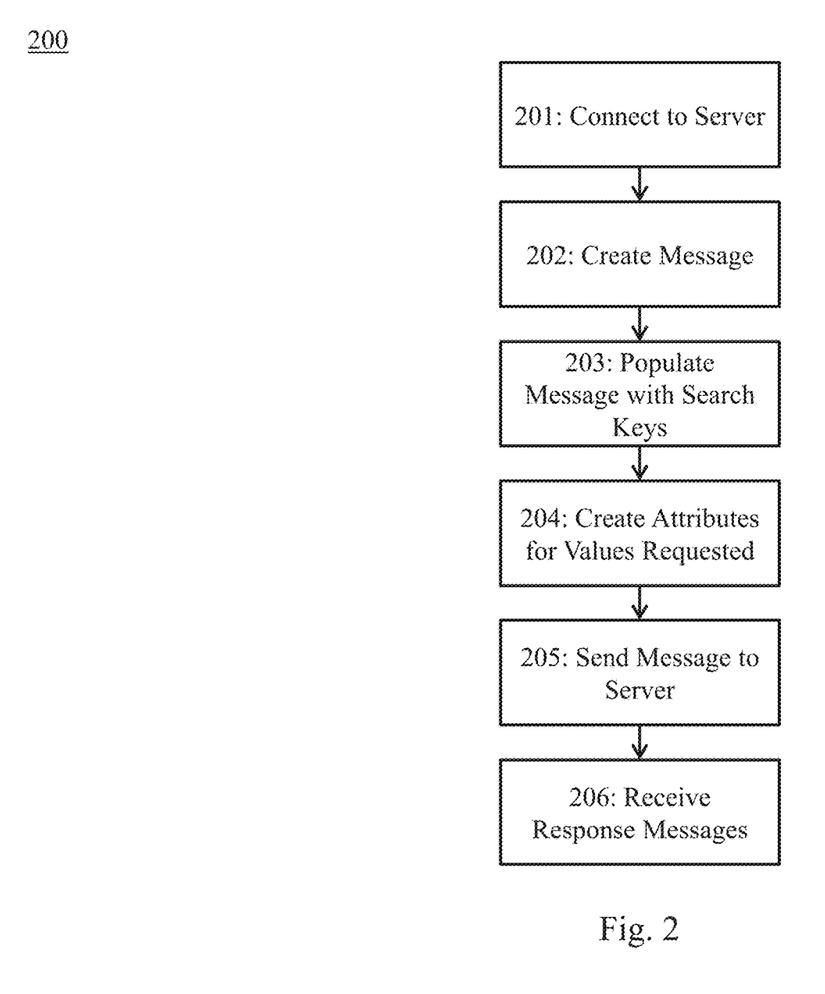
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 3:
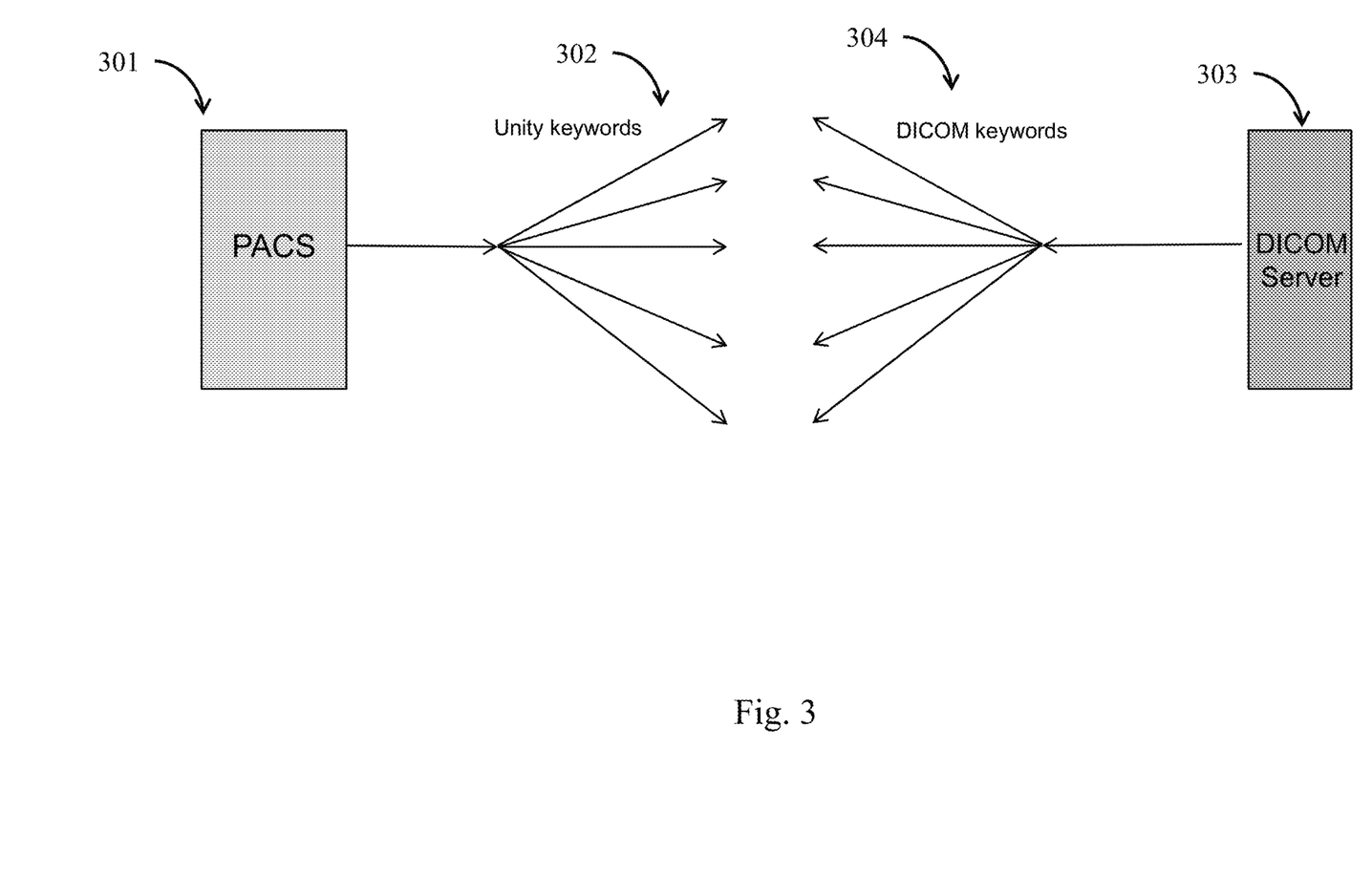
FIG. 3 is a schematic view of anatomical matching according to embodiments of the present disclosure.

Referring to FIG. 3, a schematic view of body part matching is provided according to embodiments of the present disclosure. As discussed above, there is a need to accurately and quickly retrieve (prefetch) prior exams when a new exam is scheduled. In alternative approaches, accurate prefetch methods are slow and both memory and bandwidth intensive, while fast prefetch methods are too inaccurate for practical usage.

In systems and methods according to the present disclosure, each new exam originating from a PACS 301 may have a single, unique body part. Each body part is deconstructed 302 into a set of globally unique keywords. A DICOM server 303 responds with what studies match for a current patient. In some embodiments, additional filters are applied to the study retrieval. Such filters may be on the basis of modality, contrast, 2D or 3D, date, site or facility name, whether data is available online, or whether a study includes measurements. The results are analyzed to create a list of keywords 304 from the DICOM server. Those keywords are then matched against the globally unique keywords, for example by scanning through the keyword list. Exams where there is a keyword-pair match are pre-fetched, while other matches are dropped.

In some embodiments, the body parts and keywords are defined as follows. Each exam is assumed to have an exam type (e.g., "MAMMO DIGITIZED LEFT"). The exam type description is scanned for unity keywords. The keywords (e.g., "MAMMO") are analyzed to determine a unique region or body part. In this example, the region is the breast. This region has an associated global keyword list (e.g., "BREAST", "DUCTOG*", "GALACTOG*", "MAMM*"). When subsequent pre-fetch is run, any results from the DICOM server that contain any of the keywords from this global list are considered a match. Any results without a keyword may be dropped.

In some embodiments, the above process is performed for the modality of a current exam plus any other, user defined modalities. This allows a very detailed method of choosing what to accept and what to reject for pre-fetch. Additionally, this process may be set once with an the initial configuration and allowed to run on an ongoing basis without further maintenance.

Figure 4:
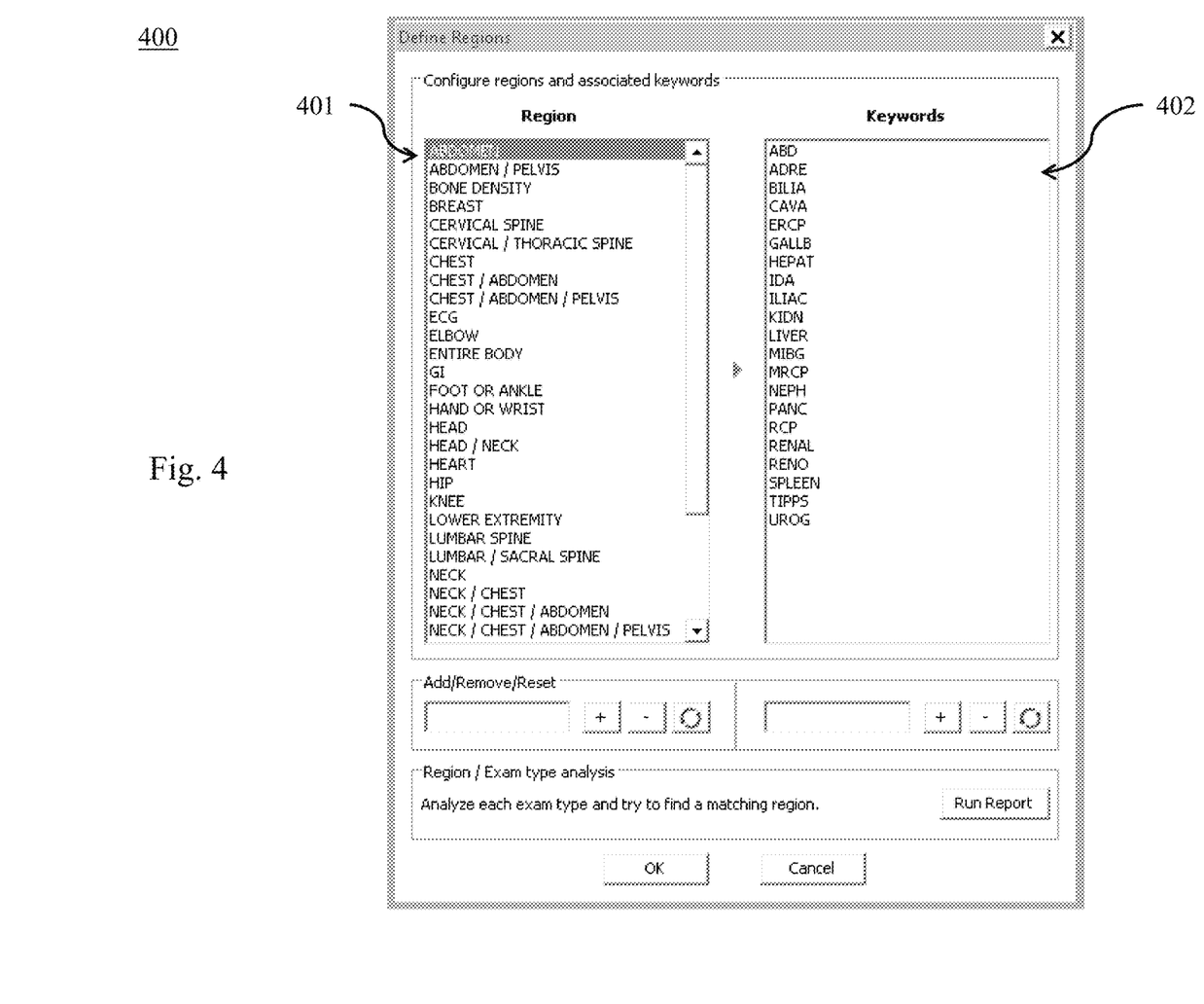
FIG. 4 depicts an exemplary user interface for the configuration of anatomical regions and associated keywords according to embodiments of the present disclosure.

Referring to FIG. 4, an exemplary user interface 400 is depicted for the configuration of anatomical regions and associated keywords. In this example, regions 401 include the abdomen. When selected, keywords 402 corresponding to the abdomen are displayed for editing.

In various embodiments, a user may add body parts, and add or remove keywords for each body part. Keywords should generally be globally unique. However, in some circustances, overlap may be permitted, such as with the term "Thora*" which may be used for both the "Thoracic Spine" body part and the "Chest" body part. In some embodiments, modalities and associated bodyparts and keywords are stored in a database.

Table 1 is a list of exemplary keywords and the associated body parts.

TABLE 1

| Body Part | Key Words |
|---|---|
| Head | Brain, head, auditor, posterior fossa, IAC, cereb, eye, pitu, CSF, tempor |
| Skull | Skull, sinus, mandib, maxil, nose, nasal, zygo, orbit, TMJ, mastoid, maxillofacial, dent, facial, crania |
| Neck | Neck, tong, laryn, parot, submand, oropharyn, nasopharyn, thyroid, carot |
| Chest | Chest, CxR, thora, lung, pulmonary, rib, sterno, |
| Abdomen | Abd, liver, hepat, spleen, pancrea, MRCP, bilia, gallbl, renal, reno, kidn, iliac, Meckels, aort, tipps, urog, cava, MIBG, IDA, |
| Pelvis | Pelv, vag, prostat, bladd, ureth, cysto, hystero, HSG, obstetr, OB_, uter, ovar, scrot, testi, |
| Cardiac | Card, heart, coronar, thall, mibi, |
| Shoulder | Shoulder, glenohumeral, acromioclav, AC_, scapul, clavic |
| Elbow | Elbow |
| Wrist/Hand | Wrist, hand, digit, fing, thumb, bone age, scaph |
| Hip | Hip, acetab, |
| Knee | Knee, patel, sunris, popli |
| Foot/Ankle | Foot, feet, ankle, toe, calcan, achil, tarsal |
| GI | Esophag, oeso, stomach, small bowel, duode, ilie, ileal, jeju, colo, anal, GI_, UGI_, Barium enema, BE_, entero, defo, fistul, loopo, cholang, swall, speech, |
| Upper Extremity | Upper ext, extremity upper, ext upper, extr upper, arm, forear, humer, radiu, ulna |
| Lower Extremity | Lower ext, extremity lower, ext upper, extr upper, thigh, leg, calf, femu, femo, tibia, fibul, length |
| Cervical Spine | Cervic, odon, c spine, c-spine |
| Thoracic Spine | Thoracic spine, t spine, t-spine |
| Lumbar Spine | Lumbar, l spine, l-spine |
| Sacrum/Coccyx | Sacrum, sacral, coccyx, |
| Breast | Breast, mamm, stereot, ductog, tomosyn, galactog, hook |
| Whole Body | Whole body, skull to thigh, skull-to-thigh, bone surv, osseous surv, scoliosis |
| DXA | Dexa, DXA, QCT, densitom |
| MISC | PICC, facet, nerve, place, NG_, sclero, thromb, ather |

Referring to FIG. 5, exemplary report output is provided. In this example, the indicated exam descriptions 501 have been matched to the indicated regions 502 according to the methods provided above.

Figure 7:
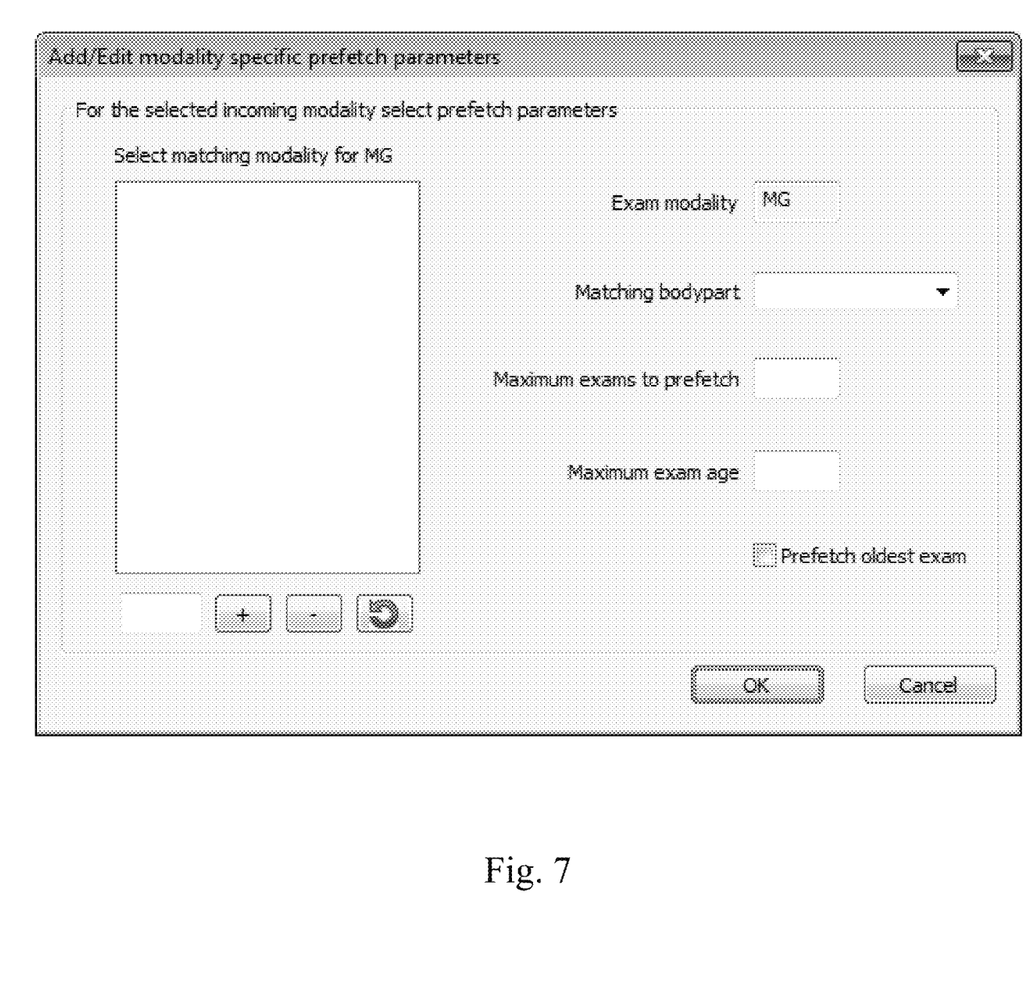
FIG. 7 depicts an exemplary user interface for configuring pre-fetch rules according to embodiments of the present disclosure.

Referring to FIG. 6-7, an exemplary user interface for configuring pre-fetch rules is provided. In FIG. 6, a list of pre-fetch rules 601 is presented. Each rule determines the regions and modalities to pre-fetch for a given exam modality of the present study. In FIG. 7, a user can input the pre-fetch rules. For a given modality, MG in this example, matching modalities, and matching body parts may be designated. In some embodiments, the prefetch rules are stored in a database table for retrieval.

Figure 8:
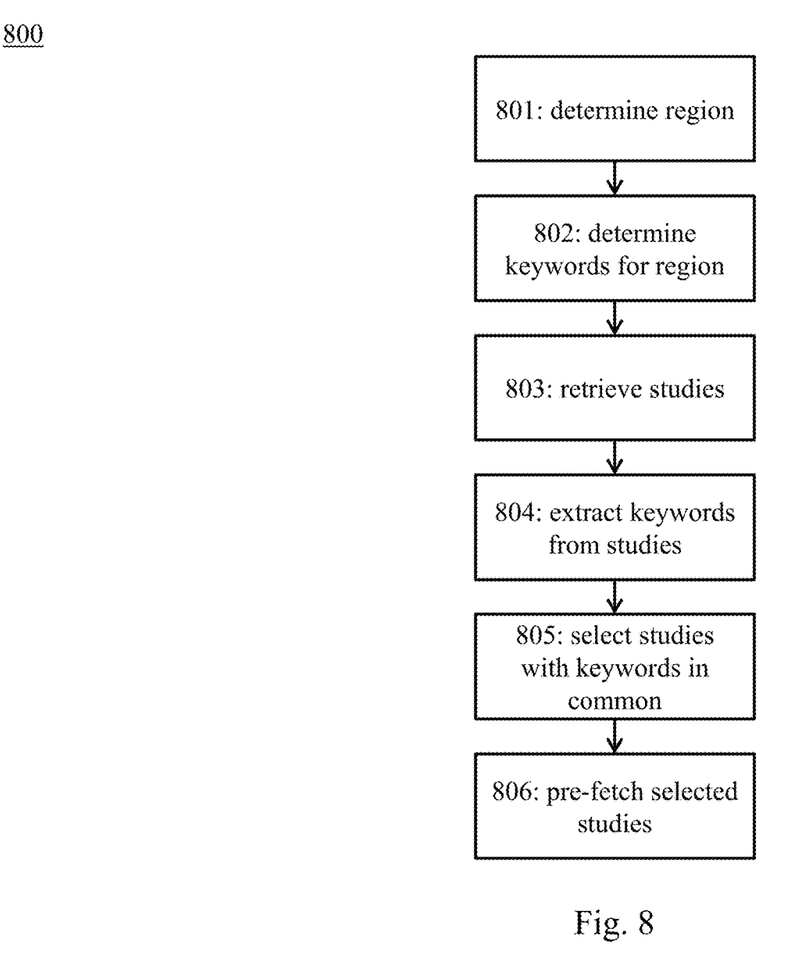
FIG. 8 illustrates a method for examination prefetching according to embodiments of the present disclosure.

Referring to FIG. 8, a method of examination prefetching is illustrated according to embodiments of the present disclosure. At 801, an anatomical region of a first medical imaging study is determined. At 802, a first plurality of keywords is determined corresponding to the anatomical region of the first medical imaging study. At 803, a plurality of studies is accessed having a patient in common with the first medical imaging study. At 804, a second plurality of keywords is extracted from the plurality of studies. At 805, those of the plurality of studies having extracted keywords in common with the first plurality of keywords are selected. At 806, the selected studies are pre-fetched for display to a user.

Figure 9:
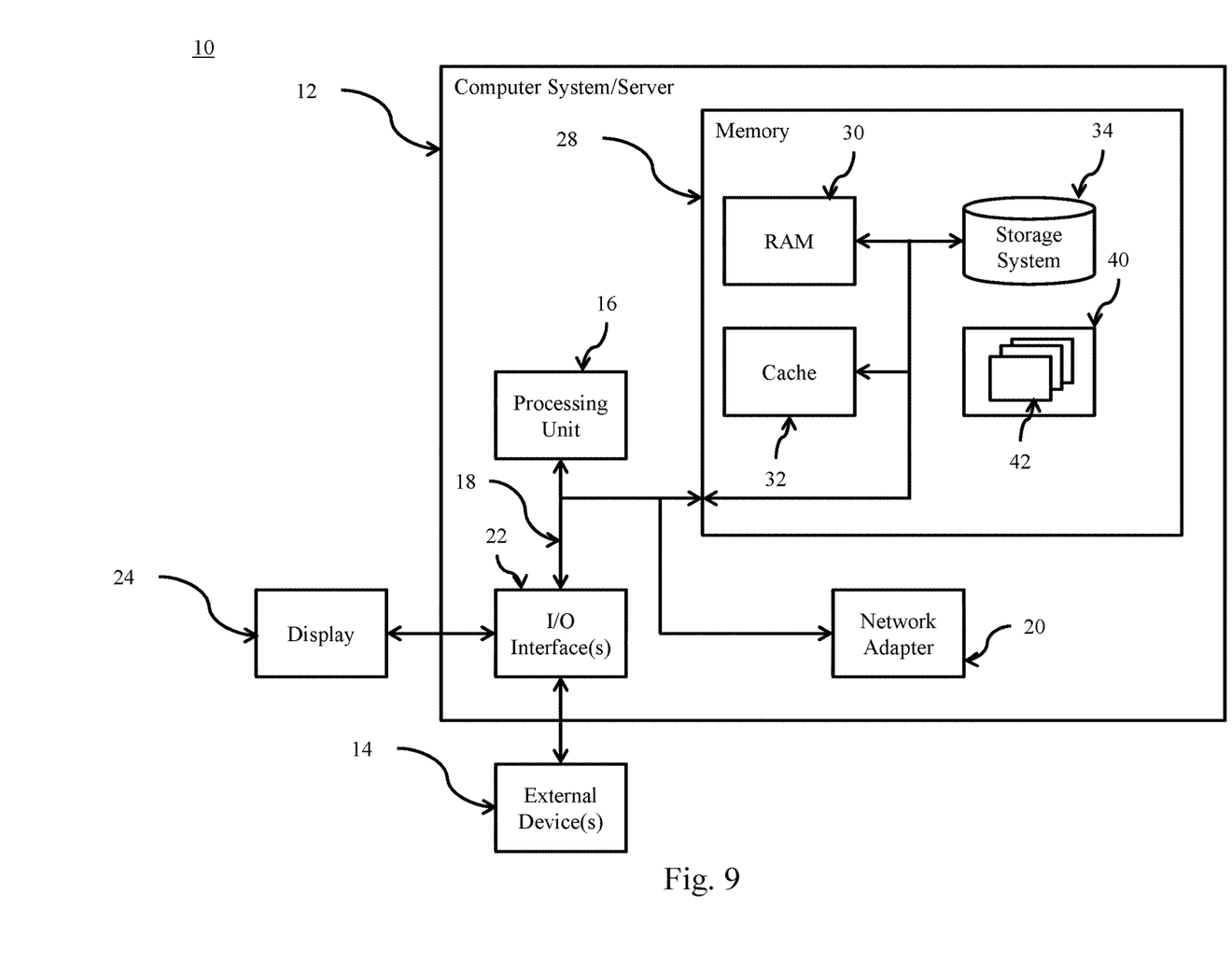
FIG. 9 depicts a computing node according to an embodiment of the present invention.

Referring now to FIG. 9, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    determining an anatomical region of a first medical imaging study, the first medical imaging study corresponding to a patient;
    after the anatomical region has been determined, determining a first plurality of keywords corresponding to the anatomical region of the first medical imaging study, wherein the first plurality of keywords comprises a name of the anatomical region supplemented with one or more additional keywords via machine learning comprising deep learning or association rule learning, the machine learning being trained to determine body part-to-keyword associations from labelled images and user corrections to the body part-to-keyword associations;
    receiving one or more rules from a user for determining one or more regions and one or more modalities to pre-fetch, the one or more rules based on a modality of the first medical imaging study, wherein the one or more rules assign each exam type of a plurality of exam types to a unique anatomical region;
    applying the one or more rules to a plurality of prior studies of the patient having occurred before the first medical imaging study, thereby filtering the plurality of prior studies to a filtered set of prior studies;
    accessing the filtered set of prior studies;
    extracting a second plurality of keywords from the filtered set of prior studies, the second plurality of keywords comprising one or more keywords extracted from each study in the filtered set of prior studies;
    for each prior study in the filtered set of prior studies, when at least one of the one or more keywords from the filtered set of prior studies are in common with at least one of the one or more additional keywords, selecting that prior study for pre-fetching thereby further filtering the filtered set of prior studies; and
    pre-fetching the any selected studies of the filtered set of prior studies for display to a user.

2. The method of claim 1, wherein the second plurality of keywords is extracted from examination descriptions of the filtered set of prior studies.

3. The method of claim 2, wherein the examination descriptions are contained in image headers.

4. The method of claim 3, wherein the image headers are DICOM headers.

5. The method of claim 1, wherein the filter is based on modality, study date, one or more DICOM attribute, 2D or 3D, or site name.

6. The method of claim 1, wherein determining the anatomical region of the first medical imaging study comprises atlas matching.

7. A computer program product for examination prefetching, the computer program product comprising a computer readable storage medium having program instructions embodied therewith, the program instructions executable by a processor to cause the processor to perform a method comprising:
- determining an anatomical region of a first medical imaging study, the first medical imaging study corresponding to a patient;
- after the anatomical region has been determined, determining a first plurality of keywords corresponding to the anatomical region of the first medical imaging study, wherein the first plurality of keywords comprises a name of the anatomical region supplemented with one or more additional keywords via machine learning comprising deep learning or association rule learning, the machine learning being trained to determine body part-to-keyword associations from labelled images and user corrections to the body part-to-keyword associations;
- receiving one or more rules from a user for determining one or more regions and one or more modalities to pre-fetch, the one or more rules based on a modality of the first medical imaging study, wherein the one or more rules assign each exam type of a plurality of exam types to a unique anatomical region;
- applying the one or more rules to a plurality of prior studies of the patient having occurred before the first medical imaging study, thereby filtering the plurality of prior studies to a filtered set of prior studies;
- accessing the filtered set of prior studies;
- extracting a second plurality of keywords from the filtered set of prior studies, the second plurality of keywords comprising one or more keywords extracted from each study in the filtered set of prior studies;
- for each prior study in the filtered set of prior studies, when at least one of the one or more keywords from the filtered set of prior studies are in common with at least one of the one or more additional keywords, selecting that prior study for pre-fetching thereby further filtering the filtered set of prior studies; and
- pre-fetching any selected studies of the filtered set of prior studies for display to a user.

8. The computer program product of claim 7, wherein the second plurality of keywords is extracted from examination descriptions of the filtered set of prior studies.

9. The computer program product of claim 8, wherein the examination descriptions are contained in image headers.

10. The computer program product of claim 9, wherein the image headers are DICOM headers.

11. The computer program product of claim 7, wherein the filter is based on modality, study date, one or more DICOM attribute, 2D or 3D, or site name.

12. The computer program product of claim 7, wherein determining the anatomical region of the first medical imaging study comprises atlas matching.

13. A system comprising:
- an image archive;
- a display;
- a computing node having program instructions embodied therewith, the program instructions executable by a processor to cause the processor to perform a method comprising:
  - determining an anatomical region of a first medical imaging study, the first medical imaging study corresponding to a patient;
  - after the anatomical region has been determined, determining a first plurality of keywords corresponding to the anatomical region of the first medical imaging study, wherein the first plurality of keywords comprises a name of the anatomical region supplemented with one or more additional keywords via machine learning comprising deep learning or association rule learning, the machine learning being trained to determine body part-to-keyword associations from labelled images and user corrections to the body part-to-keyword associations;
  - receiving one or more rules from a user for determining one or more regions and one or more modalities to pre-fetch, the one or more rules based on a modality of the first medical imaging study, wherein the one or more rules assign each exam type of a plurality of exam types to a unique anatomical region;
  - applying the one or more rules to a plurality of prior studies of the patient having occurred before the first medical imaging study, thereby filtering the plurality of prior studies to a filtered set of prior studies;
  - accessing from the image archive the filtered set of prior studies;
  - extracting a second plurality of keywords from the filtered set of prior studies, the second plurality of keywords comprising one or more keywords extracted from each study in the filtered set of prior studies;
  - for each prior study in the filtered set of prior studies, when at least one of the one or more keywords from the filtered set of prior studies are in common with at least one of the one or more additional keywords, selecting that prior study for pre-fetching thereby further filtering the filtered set of prior studies; and
  - pre-fetching from the image archive any selected studies of the filtered set of studies for display on the display.

14. The system of claim 13, wherein the second plurality of keywords is extracted from examination descriptions of the filtered set of prior studies.

15. The system of claim 14, wherein the examination descriptions are contained in image headers.

16. The system of claim 15, wherein the image headers are DICOM headers.

17. The system of claim 13, wherein determining the anatomical region of the first medical imaging study comprises atlas matching.

* * * * *